(12) United States Patent
Ploy et al.

(10) Patent No.: US 11,617,535 B2
(45) Date of Patent: *Apr. 4, 2023

(54) MEDICAL OR DENTAL DEVICE FOR DETERMINING THE QUALITY OF A BONE

(71) Applicant: W&H Dentalwerk Bürmoos GmbH, Bürmoos (AT)

(72) Inventors: Gernot Ploy, Bürmoos (AT); Wilhelm Brugger, Wals-Siezenheim (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 142 days.

This patent is subject to a terminal disclaimer.

(21) Appl. No.: 17/198,182

(22) Filed: Mar. 10, 2021

(65) Prior Publication Data

US 2021/0186413 A1  Jun. 24, 2021

Related U.S. Application Data

(63) Continuation of application No. 15/873,853, filed on Jan. 17, 2018, now Pat. No. 10,973,457, which is a continuation of application No. PCT/EP2016/066846, filed on Jul. 15, 2016.

(30) Foreign Application Priority Data

Jul. 20, 2015 (EP) .................................... 15177428

(51) Int. Cl.
*A61B 5/00* (2006.01)
*A61C 8/00* (2006.01)
(Continued)

(52) U.S. Cl.
CPC .......... *A61B 5/4504* (2013.01); *A61B 5/4547* (2013.01); *A61B 17/1655* (2013.01);
(Continued)

(58) Field of Classification Search
CPC ..... A61B 5/4504; A61B 5/4547; A61C 1/003; A61C 1/186; A61C 17/1655; A61C 8/0089; A61C 19/04
See application file for complete search history.

(56) References Cited

U.S. PATENT DOCUMENTS

2011/0245833 A1* 10/2011 Anderson ............... B23B 49/02
606/80
2015/0282895 A1* 10/2015 Theorin ............... A61C 8/0089
433/167

FOREIGN PATENT DOCUMENTS

CN   101166464 A   4/2008
EP   1842484      10/2007
(Continued)

OTHER PUBLICATIONS

Di Stefano et al., "A Possible Novel Objective Intraoperative Measurement of Maxillary Bone Density," *Minerva Stomatol*, 62(7-8):259-265 (Jul.-Aug. 2013).
(Continued)

*Primary Examiner* — Nathaniel J Kolb
(74) *Attorney, Agent, or Firm* — Klarquist Sparkman, LLP

(57) ABSTRACT

A medical or dental device for determining a bone's quality by cutting a thread into the bone with a rotating threaded element comprises a control unit having a measurement circuit configured: (i) to determine values of the motor current via a first electrical contact device with which the motor drive is supplied for rotational drive of the threaded element that can be connected to the motor drive, the current values being a measure of the bone's quality; (ii) to monitor and/or to determine the penetration depth of the threaded element into the bone, and (iii) to generate measurement signals which show the relationship between the penetration depth and the determined current values or parameters (Continued)

derived therefrom, and to transmit these signals to a display unit, which displays the relationship between the determined current values or parameters derived therefrom, in particular the bone's quality, and the penetration depth.

26 Claims, 2 Drawing Sheets

(51) Int. Cl.
*A61B 17/16* (2006.01)
*A61C 1/00* (2006.01)
*A61C 1/18* (2006.01)
*A61B 90/00* (2016.01)

(52) U.S. Cl.
CPC .............. *A61C 1/003* (2013.01); *A61C 1/186* (2013.01); *A61C 8/0089* (2013.01); *A61B 2090/066* (2016.02)

(56) References Cited

FOREIGN PATENT DOCUMENTS

| EP | 1842497 | 10/2007 |
| WO | WO00/15138 | 3/2000 |
| WO | WO2013/050851 A1 | 4/2013 |
| WO | WO2014/076653 A1 | 5/2014 |
| WO | WO2015/014771 A2 | 2/2015 |

OTHER PUBLICATIONS

Di Stefano et al, "A Torque-Measuring Micromotor Provides Operator Independent Measurements Making Four Different Density areas in Maxillae," *The Journal of Advanced Prosthodont*, 7(1):51-55, (Feb. 2015).

International Search Report for PCT/EP2016/066846 (dated Oct. 27, 2016).

Pocket Dentistry "Misch Bone Density Classification," (Apr. 2015).

* cited by examiner

MEDICAL OR DENTAL DEVICE FOR DETERMINING THE QUALITY OF A BONE

CROSS REFERENCE TO RELATED APPLICATION

This application is a continuation of U.S. patent application Ser. No. 15/873,853, filed Jan. 17, 2018, which is a U.S. bypass continuation application of International Application No. PCT/EP2016/066846, filed Jul. 15, 2016, which in turn claims priority from pending European Patent Application No. 15177428.8, filed Jul. 20, 2015, which are incorporated herein by reference.

BACKGROUND

Field

The invention relates to a medical, in particular dental or dental surgical, device for determining the quality of a bone by tapping a thread into the bone with a rotating threaded element with at least one cutting edge.

Such a device is known from the patent application WO 2014/076653 A1.

SUMMARY

It would be advantageous to create a medical, in particular dental or dental surgical device for determining the quality of a bone by cutting a thread into the bone using a rotating threaded element with at least one cutting edge, which provides the user with succinct, rapidly comprehensible information containing the most important data about the determined bone quality, in particular also including a qualitative depth profile of the bone.

Described below are implementations of devices and methods that address shortcomings of current approaches. According to one implementation, a medical, in particular dental or dental surgical, device for determining the quality of a bone by tapping a thread into the bone by a rotating threaded element having at least one cutting edge comprises a control unit which has a first electrical contact device for connection to a motor drive, a second contact device for connection to a display unit and a measurement circuit operatively connected to the first electrical contact device and the second contact device. The measurement circuit is configured or designed:

(i) to determine through the first electrical contact device values of the motor current with which the motor drive is supplied for driving the threaded element, which can be connected to the motor drive to rotate, wherein the motor current values correlate with or are substantially proportional to transmitted torque values of the motor drive, and wherein the motor current values or torque values are a measure of the quality of a bone,
(ii) to monitor and/or to ascertain the depth of penetration of the threaded element into the bone, and
(iii) to generate measurement signals, which establish a relationship between the determined values of the motor current, the torque values which correlate with the motor current values or are substantially proportional thereto or parameters derived therefrom and the depth of penetration, and to transmit these measurement signals via the second contact device to the display unit, so that the display unit shows the relationship, based on the transmitted measurement signals, between the determined motor current values, the torque values which correlate with or are substantially proportional the motor current values and/or parameters derived therefrom, in particular the quality of a bone, and the depth of penetration.

Displaying on a display unit the relationship between the determined motor current values, the torque values which correlate with or are substantially proportional the motor current values and/or parameters derived therefrom, in particular the quality of a bone, and the depth of penetration, allows the user to recognize the quality of the bone at a glance, in particular the course of or variations in bone quality with a proceeding depth of penetration and to make decisions based on this information for the next treatment steps.

The motor current values determined by the measurement circuit are a measure of the quality of the bone into which the threaded element is screwed. The quality of the bone into which the threaded element is screwed correlates in particular with the respective determined motor current values or is substantially proportional thereto and/or can be derived from the respective determined motor current values, for example, through a comparison table that is provided in the control unit or is associated with the measurement circuit and in which different motor current values are associated with different bone qualities. The control unit or the measurement circuit is thus designed in particular to compare or to show the relationship between the motor current values determined by the measurement circuit and the motor current values stored in the comparison table and/or the bone qualities.

The first electrical contact device for connection to a motor drive is preferably connected to the motor drive by at least one supply line or control line. The first electrical contact device is preferably designed as a releasable connection. A coupling connection for connection, in particular via the at least one power supply or control line, to the first electrical contact device is preferably provided on the motor drive. The first electrical contact device preferably comprises a plurality of electrical contacts which are connected to electrical contacts on the motor drive, in particular through the at least one supply or control line.

The second contact device for connection to a display unit is designed as a hardwired, in particular releasable, contact device, for example. Preferably at least one power supply or control line, over which the aforementioned measurement signals of the measurement circuit in particular can be transmitted to the display unit, connects the second contact device to the display unit or to a contact device provided on the display unit. The measurement signals comprise in particular electrical signals so that the second contact device and the contact device of the display unit are especially preferably designed as electrical contact devices.

Alternatively, the second contact device is designed for connection to a display unit as a wireless contact device, in particular for transmitting electromagnetic waves, for example, radio waves. The second contact device preferably thus comprises at least one transmitting unit, and the display unit includes at least one receiving unit, so that the aforementioned measurement signals of the measurement circuit or the electromagnetic waves based thereon can be transmitted to the display unit. The second contact device also comprises in particular a converter unit for converting the electrical measurement signals of the measurement circuit into electromagnetic waves, in particular radio waves.

The measurement circuit is preferably implemented by a microprocessor and corresponding software. However, it is also conceivable to design the measurement circuit through hardware, in particular logic modules, or by through combination of a microprocessor with software and hardware. The microprocessor or microcontroller is especially preferably part of the control unit and comprises in particular additional control or regulating circuits, for example, for controlling or regulating the motor drive and/or the display unit and/or for processing of signals that can be generated, in particular by the user, through one or more operating elements or actuating elements. The operating elements or actuating elements are in particular part of the medical, in particular dental, device and are provided, for example, on the control unit and/or on the display unit and/or are connected thereto.

The determination of the depth of penetration (the advancing penetration) of the threaded element into the bone can be achieved by various devices and methods, for example, by an optical measurement/optical measurement device or by an impedance measurement/an impedance measurement device or through sound/a sound-measuring device. All these alternative embodiments however require additional components, for example, radiation, sound or electric current sources so that implementation in a device for determination of the bone quality is technically complicated and expensive. The determination of the depth of penetration of the threaded element into the bone described in this document has the great advantage in comparison with other possible methods that no additional components are required but instead it can be carried out exclusively with components that are necessary or present anyway for tapping the thread.

Determination of the depth of penetration (the advancing penetration) of the threaded element into the bone is thus preferably based on at least one parameter and/or measured value of at least one element of the medical, in particular dental, device for determination of the bone quality, which is necessary for cutting a thread with a rotating threaded element driven by a motor drive into the bone. In particular, the depth of penetration of the threaded element into the bone can be determined on the basis of at least one parameter and/or measured value of at least one of the following elements: the motor drive, a gear unit disposed between the motor drive and the threaded element, in particular in a handpiece, or the threaded element for cutting a thread into the bone.

The measurement circuit is preferably designed to process values of an angle of rotation of a rotor, in particular a magnetic rotor of the motor drive in order to monitor and/or determine the depth of penetration of the threaded element into the bone. The values of an angle of rotation of the rotor can be determined, for example, by angle of rotation—sensors assigned to the rotor, for example, by Hall-sensors. Alternatively, the values of an angle of rotation in the case of a sensorless motor drive can be determined, for example, through energization of the coils or through short-term output of high-voltage pulses to the windings of a stator of the motor drive.

It is also conceivable to operate the motor drive at a constant rotational speed so that it is not necessary to measure the angle of rotation values of the rotor but alternatively, a fixed or predetermined angle of rotation value is stored in the control unit, in particular in a memory and can be transmitted to the measurement circuit.

The measurement circuit is preferably designed to take into account or to process the transmission ratio, in particular including the degree of efficiency, of a gear unit of the medical, in particular dental, device arranged between the motor drive and the threaded element in order to monitor and/or determine the depth of penetration of the threaded element into the bone in order. The gear unit preferably comprises two intermeshing gearwheels. The gear unit preferably comprises a reduction gear. The gear unit is preferably arranged in a handpiece, on which a holding device for the threaded element is also provided in particular.

The transmission ratio of the gear unit, in particular including the degree of efficiency, is preferably stored in the control unit, in particular in a memory and can be transmitted to the measurement circuit or queried by the measurement circuit. Alternatively, the transmission ratio of the gear unit, in particular including the degree of efficiency, is stored in a memory element associated with or provided on the gear unit or the handpiece and can be queried by the control unit or the measurement circuit and can be transmitted directly or via a memory of the control unit to the measurement circuit.

The measurement circuit is preferably designed to take into account at least one property of the threaded element, for example, the slope of the at least one cutting edge, the shape of the cutting edge or the outer shape of the threaded element in order to monitor and/or determine the depth of penetration of the threaded element into the bone. The cutting edge of the threaded element is designed in particular as a cutting element having a threaded shape.

The at least one property of the threaded element is preferably stored in the control unit, in particular in a memory, and can be transmitted to the measurement circuit or can be queried by the measurement circuit. Alternatively, the at least one property of the threaded element is stored in a memory element assigned to the threaded element or provided thereon and can be queried by the control unit or the measurement circuit and can be transmitted to the measurement circuit either directly or via a memory of the control unit.

The measurement circuit is preferably designed to process and/or combine multiple or all measured values, parameters or properties referred to above in order to monitor and/or determine the depth of penetration (of the advancing penetration) of the threaded element into the bone. In particular the measurement circuit is designed to process at least one measured value, parameter or property of each of the motor drive, the gear unit and the threaded element in order to monitor and/or determine the depth of penetration of the threaded element into the bone. It is thus advantageously possible to make a particularly accurate determination of the depth of penetration. The measurement circuit in particular preferably calculates the depth of penetration of the threaded element into the bone by using the following equation:

$$D = \frac{S \times A}{T}$$

where D=the depth of penetration of the threaded element into the bone, S=the slope of the at least one cutting edge of the threaded element, A=the angle of rotation of the motor drive and T=the transmission ratio of the gear unit.

At least one predetermined depth of penetration is preferably stored in the control unit, for example, 6 mm or 8 mm. Alternatively, several predetermined depths of penetration are stored in the control unit, which can be selected by the user through an operating element of the device for determining the bone quality or the control unit. The control unit, for example, the measurement circuit or some other circuit, is especially preferably designed to compare the monitored and/or determined depth of penetration of the threaded element with the at least one predetermined depth of penetration in order to stop the motor drive and/or change its direction of rotation on reaching or exceeding the at least one predetermined depth of penetration.

The control unit, in particular the measurement circuit, is preferably designed to begin the monitoring and/or determination or a recording or storage of the depth of penetration (of the progressive penetration) of the threaded element into the bone only after reaching or exceeding a predetermined motor current threshold or torque threshold. This ensures a reliable determination of the depth of penetration of the threaded element because by reaching or exceeding the predetermined motor current threshold/torque threshold, it is ensured that the threaded element will in fact cut a thread and/or penetrate into the bone. The predetermined motor current threshold/torque threshold is preferably stored in the control unit, in particular in a memory. The predetermined motor current threshold/torque threshold preferably cannot be altered by a user. The control unit, in particular the measurement circuit, is preferably designed to repeatedly compare the instantaneous motor current value/torque value determined by the measurement circuit with the predetermined motor current threshold/torque threshold until reaching the predetermined motor current threshold/torque threshold.

The medical, in particular dental or dental surgical device preferably comprises a display unit which is connected communicatively to the second contact device and which shows the relationship between the determined motor current values, the torque values which correlate with or are substantially proportional to the motor current values and/or parameters derived therefrom, in particular the quality of a bone, and the depth of penetration, and in particular represents them graphically. The display unit comprises in particular a screen or a monitor. The display unit is optionally designed as a separate unit, which is connected operatively to the control unit, in particular wirelessly through the second wireless contact device described above, or is designed as an integral part of the control unit.

The display unit shows the relation between the determined motor current values, the torque values which correlate with or are substantially proportional the motor current values and/or parameters derived therefrom, in particular the quality of a bone, and the depth of penetration, in particular the qualitative depth profile of the bone, preferably represented graphically in the form of a diagram or a schematic representation of a bone structure having a layered structure in particular.

The diagram or the schematic representation is preferably designed so that a motor current value, a torque value correlating with or substantially proportional to the motor current value and/or a parameter derived therefrom, in particular the quality of the bone, is/are assigned to each (individual) value for the depth of penetration. The motor current value, the torque value and/or a parameter derived therefrom, in particular the quality of the bone, assigned to each individual value of the depth of penetration may either also comprise a single value or averaged or combined values of several determined motor current values, torque values and/or parameters derived therefrom, in particular the quality of the bone. The combined values comprise, for example, different classes of bone qualities, for example, bone quality class 1, bone quality class 2, bone quality class 3, etc.

Accordingly, the display unit is preferably designed to display a diagram or a schematic representation on the basis of the measurement signals of the measurement circuit, such that a single value of the determined motor current, a torque value which correlates with or is substantially proportional thereto and/or a parameter derived therefrom, in particular the quality of the bone, is assigned to each (individual) value of the depth of penetration. Alternatively, the display unit is designed to display a diagram or a schematic representation on the basis of the measurement signals of the measurement circuit, such that to each (individual) value of the depth of penetration averaged or combined values of multiple determined motor current values, torque values and/or parameters derived therefrom, in particular the quality of a bone, are assigned.

The diagram displayed by the display unit is preferably designed as a two-dimensional diagram plotting in particular the depth of penetration (in mm) on the abscissa and plotting the motor current value, the torque value which correlates with or is substantially proportional to the motor current value and/or a parameter derived therefrom, in particular the quality of a bone on the ordinate. The diagram is preferably embodied as a line diagram but of course any other type of diagram may also be used, for example, a bar chart, a bar graph or a scatter chart.

The schematic diagram of a bone structure, in particular a structure in layers displayed by the display unit is preferably embodied as a two-dimensional representation, with the depth of penetration (in mm) being plotted on its ordinate in particular. Preferably horizontal bars or strips extend from the ordinate representing average or combined values of multiple determined motor current values, torque values which correlate with or are essential proportional to the motor current values, and/or parameters derived therefrom, in particular the quality of the bone. The horizontal bars or strips especially preferably have different markings or colors.

The medical, in particular dental, device for determining the quality of the bone preferably also comprises a motor drive and a handle element which is or can be connected to the threaded element and which is connectable to or comprises the motor drive. The motor drive is preferably designed as an electric motor drive, for example, as a brushless electric motor. The handle element is preferably designed as an angled handpiece or a contra-angle handpiece. A holding device, in particular a releasable chuck device, for the threaded element is preferably provided on the handpiece, in particular on its front end or head part. A lighting device for illuminating the preparation site with visible light is preferably provided on the handpiece, in particular on its front end or head part.

The medical, in particular dental, device for determining the bone quality, in particular the control unit preferably comprises at least one memory element, in which at least the instantaneous measured values of the determined motor current values, of the torque values which correlate with or are substantially proportional to the motor current values or parameters derived therefrom, in particular the quality of the bone, and the depth of penetration can be saved.

The control unit preferably comprises an evaluation circuit which is designed to compare with comparative values for determining the quality of a bone and/or combine into bone quality classes and/or assign to bone quality classes at least one of: the motor current values determined by the measurement circuit; the torque values which correlate with the motor current values or are substantially proportional thereto; parameters derived therefrom. The evaluation circuit is preferably at least communicatively connected to the measurement circuit for receiving the measurement signals or is designed as part of the measurement circuit. The evaluation circuit is preferably connected to the display unit, so that the display unit can display data, in particular bone quality classes, that has been processed, compared or combined by the evaluation unit.

The control unit, for example, the measurement circuit or the evaluation circuit, is preferably additionally designed to determine the course and/or the integrated data of the energy or power required or expended by the motor drive during the cutting of the thread in a bone and to transmit a corresponding display signal to the display unit via the second contact device on the basis of the display signal transmitted, so that the display unit displays, on the basis of the display signal transmitted, the energy or power required or expended during the cutting of the thread. The control unit preferably calculates the required or expended energy or power based on the course or the integration of the determined motor current values or the torque values derived therefrom, the maximum depth of penetration and/or the angle of rotation, the time required until reaching the maximum depth of penetration and optionally the rotational speed of the rotating threaded element to be determined.

The rotating threaded element preferably comprises a thread cutter or an implant, in particular a self-tapping implant. The rotating threaded element comprises at least one cutting element that extends in a coil or spiral shape around a body of the threaded element, in particular a cutting thread that cuts into a bone.

These and other embodiments will be described below with reference to the following drawings.

DETAILED DESCRIPTION

Figure 1:
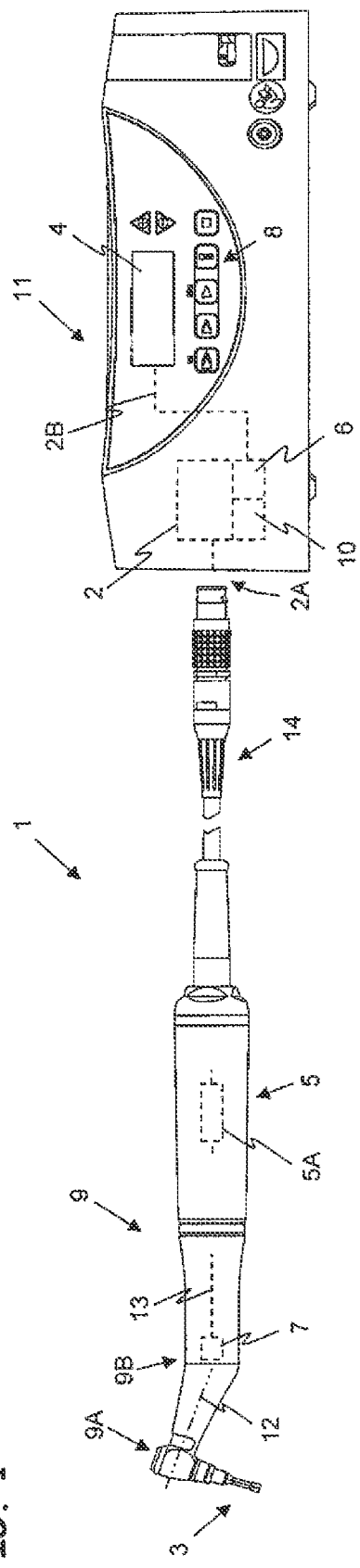
FIG. 1 shows a medical, in particular dental or dental surgical, device for determining the quality of a bone, having a handle element, a threaded element and an operating and/or control console.

The medical, in particular dental or dental surgical, device 1, shown in FIG. 1, for determining the quality of a bone, in particular a jawbone, comprises a handle element 9, a rotating threaded element 3 with at least one cutting edge, a motor drive 5, in particular an electric motor drive, and a control unit 2 with a measurement circuit 6.

The handle element 9 designed as a contra-angle handpiece comprises a head section 9A and a handle section 9B with a longitudinal axis 12. The rotating thread element 3 is attached to the head section 9A in such a way, in particular in a releasable receptacle or holding device, that it is arranged at an angle to the longitudinal axis 12 of the handle section 9B.

At least one or more in particular rotatable drive shafts 13 and a gear unit 7, in particular with a reduction gear are provided in the handle element 9. The at least one drive shaft 13 and the gear unit 7 are in particular connected to one another and to the motor drive 5 in such a way that a rotating movement of the motor drive 5 can be transmitted via the driveshaft 13 and the gear unit 7 to the rotating or rotatable threaded element 3.

The (electric) motor drive 5 or electric motor is provided for driving the rotatable threaded element 3, the at least one rotatable driveshaft 13 and the gear unit 7. The motor drive 5 is preferably an independent component which can be connected releasably to the handle element 9 and/or to the at least one rotatable driveshaft 13, for example, by a coupling device. Alternatively, the motor drive 5 is designed as part of the handle element 9. The (electric) motor drive 5 comprises in particular a stator, a rotor 5A that can be moved relative thereto and has at least one magnetic element, and at least one motor shaft which can be coupled or is connected to the driveshaft 13 of the handle element 9.

The motor drive 5 and the handle element 9 are preferably connected to an operating and/or control console 11 via a supply tubing 14. At least one supply line or control line is provided in the supply tubing 14, or in particular multiple electrical conductors are provided therein for transmitting driving energy for the motor drive 5 and for transmitting control, regulating or measurement signals, preferably also for transmitting power for a lighting device. The supply tubing 14 is detachably connected to the operating and/or control console 11, for example, and is releasably or non-detachably for a user connected to the motor drive 5.

As can be seen from FIG. 1, a control unit 2 comprising at least one measurement circuit 6 and preferably also an evaluation circuit 10 is provided in the operating and/or control console 11. In addition to these two circuits 6, 10, preferably at least one additional circuit and/or at least one element of the device 1 is provided in the console 11, for example, a control or regulating circuit of the motor drive 5; a comparative circuit, for example, as part of the evaluation circuit 10 which is designed to compare the motor current values which are determined by the measurement circuit, the torque values which correlate with or are substantially proportional to the motor current values or parameters derived therefrom with comparative values for determining the quality of a bone; a display unit 4; at least one operating or actuating element 8 for adjusting or selecting operating parameters; a circuit, in particular a circuit connected to the at least one operating element or actuating element 8, for operating or adjusting operating parameters for the device 1 and/or for the electric motor drive 5: a memory unit, in which measurement signals, motor current values, torque values which correlate with or are substantially proportional to the motor current values, parameters derived therefrom, in particular the quality of a bone, and/or values of the depth of penetration can be stored.

Alternatively, the measurement circuit 6, preferably also the evaluation circuit 10 and at least one of the additional circuits or elements cited above is/are provided on the handle element 9 and/or on the motor drive 5, so that the device 1 for determining the quality of the bone is designed as a wireless handle element.

The control unit 2, in particular the measurement circuit 6, is operatively connected to a first electrical contact device 2A, for example, through electrical lines, and a second contact device 2B which is preferably also an electric contact device. The first electrical contact device 2A connects the control unit 2 or the measurement circuit 6 to the motor drive 5, in particular via the supply tubing 14 and/or at least one supply line or control line. The second electrical contact device 2B connects the control unit 2 or the measurement circuit 6 to the display unit 4. The contact devices 2A, 2B are preferably part of the operating console and/or control console 11.

The measurement circuit 6 is designed, configured or programmed to determine values of the motor current via the first electrical contact device 2A, supplied to the motor drive 5 for rotationally driving the threaded element 3 which can be connected to the motor drive 5. Since the motor current values correlate with or are substantially proportional to the transmitted torque values of the motor drive 5, and since the motor current values or torque values are a measure of the quality of a bone, the measurement circuit 6 is thus designed to determine the bone quality, in particular while driving the rotating threaded element 3 or during the penetration of the rotating threaded element 3 into the bone.

The measurement circuit 6 is additionally designed to monitor and/or determine the depth of penetration (i.e., the advance of penetration) of the threaded element 3 into the bone. To do so, the measurement circuit 6, for example, processes angle of rotation values of the rotor 5A of the motor drive 5 and/or the transmission ratio, including in particular the degree of efficiency, of the gear unit 7 of the handle element 9 and/or at least one feature of the rotating threaded element 3, for example, the slope of the at least one cutting edge, the shape of the cutting edge or the outside shape of the threaded element 3.

Finally the measurement circuit 6 is designed to generate measurement signals which establish a relationship between the determined motor current values, the torque values which correlate with or are substantially proportional to the motor current values or parameters derived therefrom and the depth of penetration and to transmit these measurement signals to the display unit 4 via the second contact device 2B.

The display unit 4 is designed to display the relationship between the determined motor current values, the torque values which correlate with or are substantially proportional to the motor current values and/or parameters derived therefrom, in particular the quality of a bone, and the depth of penetration, in particular the qualitative depth profile of the bone, on the basis of the measurement signals transmitted by the measurement circuit 6. The display unit 4 in particular comprises a display screen integrated into the housing of the operating and/or control console 11, where diagrams or graphical displays can be shown. The display unit 4 is preferably also designed for display of operating parameters of the device 1 and/or a parameter that can be varied by the operating or control element 8.

Preferably at least one predetermined depth of penetration of the rotating threaded element 3 into the bone is stored in the control unit 2, in particular in a memory element. The control unit 2 is preferably designed to compare the monitored and/or determined depth of penetration of the threaded element 3 with the at least one predetermined depth of penetration and, on reaching or exceeding the at least one predetermined depth of penetration, to stop the motor drive 5 and/or to change its direction of rotation.

The evaluation circuit 10 being a part of the control unit 2 or of the measurement circuit 6 is designed, configured or programmed to compare the motor current values determined by the measurement circuit 6, the torque values which correlate with or are substantially proportional to the motor current values or parameters derived therefrom with comparative values for determining the quality of a bone and/or to combine them into bone quality classes and/or to assign them to bone quality classes. The evaluation circuit 10 is communicatively connected to the display unit 4, so that the values compared by the evaluation circuit 10 and/or the bone qualities and/or the bone quality classes can be displayed by or on the display unit 4.

The control or regulating circuit of the motor drive or electric motor 5 mentioned above is designed to control or regulate the motor drive 5 through electrical signals via the supply tubing 14 or the at least one power supply line or control line. If necessary, the control or regulating circuit is also provided to operate the motor drive 5 at a predetermined or fixed rotational speed value.

Preferably all of the circuitries and circuits 6, 10 mentioned above are embodied at electronic circuits, in particular as part of a microprocessor.

Figure 2:
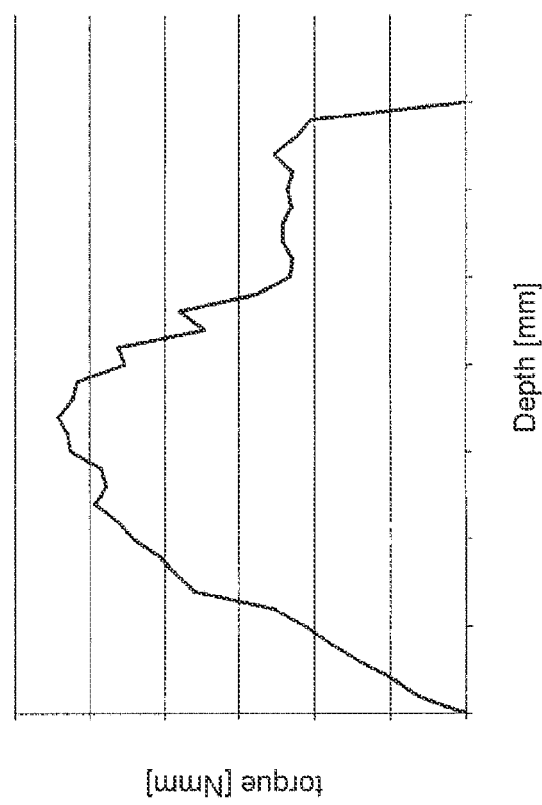
FIG. 2 shows a first embodiment of a diagram that can be displayed by the display unit and shows the relationship between the determined torque values, which correlate with or are substantially proportional to the determined motor current values, and the depth of penetration, in particular the qualitative depth profile of the bone.

FIG. 2 shows a two-dimensional diagram which can be displayed by the display unit 4 and which shows the relationship between the determined torque values which correlate with or are substantially proportional to the determined motor current values and the depth of penetration. The depth of penetration (preferably in mm) is plotted on the abscissa of the diagram and the torque values (preferably in N/mm or N/cm) are plotted on the ordinate. The diagram is embodied as a line diagram wherein a (separate) torque value is assigned to each individual value for the depth of penetration. Thus the user can read for each value of the depth of penetration the torque value determined by the measurement circuit 6 and/or can estimate the quality of the bone therefrom because, as already described above, the motor current values determined by the measurement circuit 6 or the torque values which correlate or are substantially proportional therewith provide a measure of the bone quality (the higher the motor current values or the torque values, the higher or better is the quality of the bone).

Figure 3:
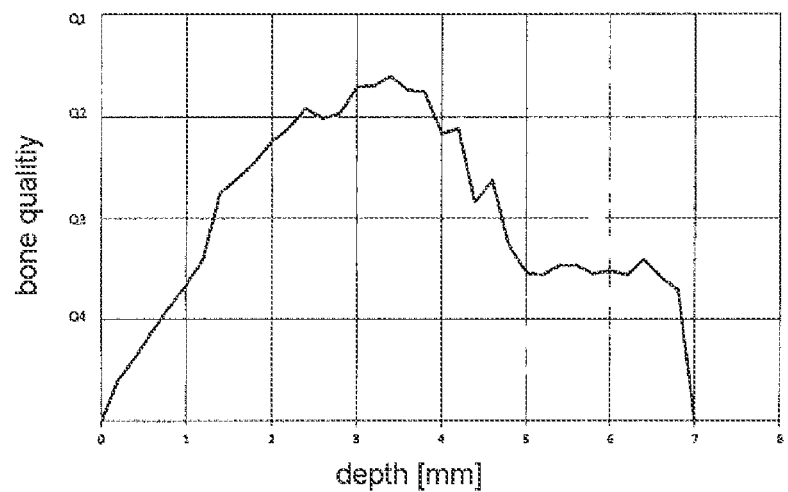
FIG. 3 shows a second embodiment of a diagram that can be displayed by the display unit and shows the relationship between the bone quality, based on the determined motor current values, and the depth of penetration, in particular the qualitative depth profile of the bone.

FIG. 3 shows a two-dimensional diagram, which can be displayed by the display unit 4 and which shows the relationship between the bone quality, which can be derived from the torque values determined by the measurement circuit 6 or the motor current values which are determined and correlate with the torque values or are substantially proportional to them, and the depth of penetration. The depth of penetration (preferably in mm) is plotted on the abscissa of the diagram and the bone quality is plotted on the ordinate. The diagram is in turn embodied as a line diagram, wherein a bone quality class is assigned to each individual value of the depth of penetration. Thus the user can read the bone quality or bone quality class for each value of the depth of penetration.

The diagram in FIG. 3 comprises, for example, four bone quality classes Q1-Q4, but of course more or fewer bone quality classes are also conceivable, for example, two, three, five, six or more bone quality classes. Each bone quality class comprises or represents a predefined range of motor current values determined by the measurement circuit 6 or torque values which correlate with or are substantially proportional thereto. Thus, for example, the bone quality class Q4 comprises torque values of 8.00 Ncm-6.00 Ncm, the bone quality class Q3 comprises torque values of 5.99 Ncm-4.00 Ncm, etc. Accordingly the bone quality shown in the diagram in FIG. 3 is high at a low depth of penetration and at a greatly progressed depth of penetration, i.e., the bone is hard and the bone quality is low in the range of the medium depth of penetration, i.e., the bone is soft.

Figure 4:
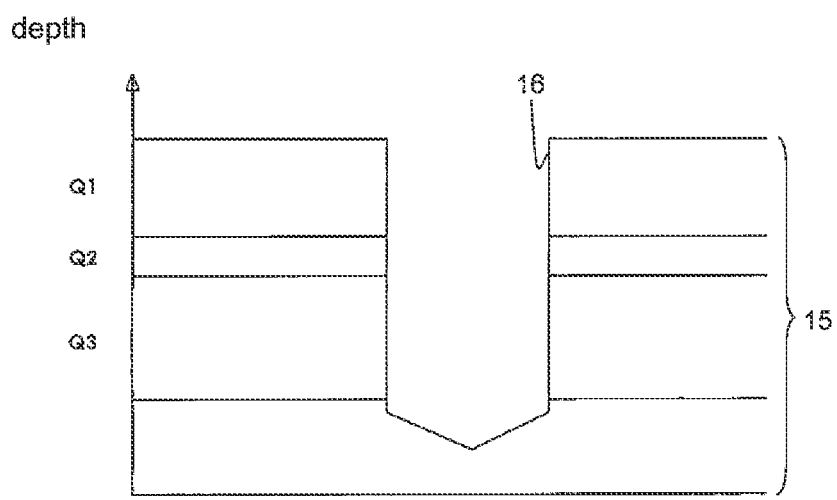
FIG. 4 shows an embodiment of a diagram that can be displayed by the display unit and shows the relationship between the bone quality, based on the determined motor current values, and the depth of penetration, in particular the qualitative depth profile of the bone, on a schematically represented bone structure.

FIG. 4 shows an embodiment of a diagram, in particular a two-dimensional diagram, which can be displayed by the display unit 4, and which reflects the relationship between the bone quality, based on the motor current values determined by the measurement circuit 6, and the depth of penetration on a schematically diagramed bone structure 15. The bone structure 15 also shows a borehole 16, likewise schematically, representing in particular the borehole into which the threaded element 3 of the medical, in particular dental or dental surgical device 1 cuts a thread.

The depth of penetration (in mm) is plotted on the ordinate in the diagram in FIG. 4. Horizontal bars or strips representing the quality of the bone in the form of bone quality classes extend from the ordinate. Even with this type of display, a bone quality class can still be assigned to each individual value of the depth of penetration.

Each bone quality class comprises or represents a predefined range of motor current values determined by the measurement circuit 6 or torque values which correlate or are substantially proportional therewith, as described in conjunction with the diagram in FIG. 3. The horizontal bars or strips especially preferably have different marks or colors, in particular a separate mark or color being assigned to each bone quality class. For example, the diagram of FIG. 4 comprises three bone quality classes Q1-Q3, but of course more or fewer bone quality classes are also conceivable here, for example, two, four, five, six or more bone quality classes. The diagram according to FIG. 4 provides the user with a particularly rapidly absorbable and readily understandable insight about the course of bone quality along the depth of penetration.

The invention is not limited to the described embodiments but instead includes all embodiments that use or include the basic appropriate function principle of the invention according to the claims. In addition all the features of all the embodiments described and illustrated here can be combined with one another.

What is claimed is:

1. A medical or dental device for determining a quality of a bone by cutting a thread into the bone by a rotating threaded element having at least one cutting edge, wherein the medical or dental device comprises:
    a control unit which comprises
    a first electrical contact device for connection to a motor drive,
    a second contact device for connection to a display unit, and
    a measurement circuit, which is operatively connected to the first electrical contact device and to the second contact device, wherein the measurement circuit is configured:
    (i) to determine values of the motor current via the first electrical contact device, the motor current being supplied to the motor drive to rotatably drive the threaded element that can be connected to the motor drive, wherein the motor current values correlate with or are substantially proportional to transmitted torque values of the motor drive, and wherein the motor current values or torque values are a measure of the quality of the bone,
    (ii) to monitor or determine the depth of penetration of the threaded element into the bone, and
    (iii) to generate measurement signals which show the relationship between the depth of penetration and at least one of: the determined motor current values, the torque values which correlate with or are substantially proportional to the motor current values, parameters derived from the determined motor current values or parameters derived from the torque values, and to transmit the measurement signals via the second contact device to the display unit, so that the display unit displays on the basis of the transmitted measurement signals the relationship between the depth of penetration and at least one of: the determined motor current values, the torque values which correlate with or are substantially proportional to the motor current values, parameters derived from the determined motor current values or parameters derived from the torque values,
    wherein the control unit is configured to start the monitoring or determination or recording of the depth of penetration of the threaded element into the bone at the beginning of the penetration of the threaded element into the bone and reaching or exceeding a predetermined motor current threshold or torque threshold.

2. The medical or dental device according to claim 1, wherein the measurement circuit is configured to process angle of rotation values of a rotor of the motor drive in order to monitor or determine the depth of penetration of the threaded element into the bone.

3. The medical or dental device according to claim 1, wherein the measurement circuit is configured to take into account the transmission ratio of a gear unit arranged between the motor drive and the threaded element of the medical or dental device in order to monitor or determine the depth of penetration of the threaded element into the bone.

4. The medical or dental device according to claim 1, wherein the measurement circuit is configured to take into account at least one property of the threaded element in order to monitor or determine the depth of penetration of the threaded element into the bone, wherein at least one property of the threaded element comprises at least one of: the slope of the at least one cutting edge of the threaded element, the shape of the cutting edge or the outer shape of the cutting element.

5. The medical or dental device according to claim 1, wherein at least one predetermined depth of penetration is stored in the control unit.

6. The medical or dental device according to claim 5, wherein the control unit is configured to compare the monitored or determined depth of penetration of the threaded element with the at least one predetermined depth of penetration and, on reaching or exceeding the at least one predetermined depth of penetration, to stop the motor drive or to change its direction of rotation.

7. The medical or dental device according to claim 1, wherein a plurality of predetermined depths of penetration are stored in the control unit which can be selected by the user through an actuating element.

8. The medical or dental device according to claim 1, further comprising a display unit that is communicatively connected to the second contact device and which displays the relationship between the depth of penetration and at least one of: the determined motor current values, the torque values which correlate with or are substantially proportional the motor current values, parameters derived from the determined motor current values or parameters derived from the torque values.

9. The medical or dental device according to claim 8, wherein the display unit depicts a schematic representation of a bone structure on which the depth of penetration and one of the parameters derived from the motor current values or parameters from the torque values are shown.

10. The medical or dental device according to claim 8, wherein the display unit is configured to display a diagram or a schematic representation on the basis of the measurement signals of the measurement circuit such that at least one of: a value of the determined motor current, a torque value that correlates with or is substantially proportional therewith, a parameter derived from the determined motor current value or a parameter derived from the torque value is assigned to each value of the depth of penetration.

11. The medical or dental device according to claim 8, wherein the display unit is configured to display a diagram or a schematic representation on the basis of the measurement signals of the measurement circuit such that averaged or combined values of at least one of: a plurality of determined motor current values, a plurality of torque values correlating with or substantially proportional to the motor current values, or a plurality of parameters derived from the torque values are assigned to the values for the depth of penetration.

12. The medical or dental device according to claim 1, wherein the device additionally comprises a motor drive and a handle element connectable to the threaded element and which is connectable to the motor drive or comprises the motor drive.

13. The medical or dental device according to claim 1, wherein the control unit comprises an evaluation circuit which is configured to compare the motor current values determined by the measurement circuit, the torque values which correlate with or are substantially proportional to the motor current values, parameters derived from the motor current values or parameters derived from the torque values with comparative values for determining the quality of a bone or to assign them into bone quality classes.

14. The medical or dental device according to claim 1, wherein the control unit is additionally configured to determine the energy, work or power required or expended by the motor drive during the cutting of the thread in a bone and to transmit a corresponding display signal via the second contact device to the display unit, so that the display unit displays the energy, work or power required or expended during the cutting of the thread on the basis of the transmitted display signal.

15. The medical or dental device according to claim 1, wherein the rotating threaded element comprises a thread cutter or an implant.

16. The medical or dental device according to claim 1, wherein the parameters derived from the determined motor current values or the torque values comprise the quality of the bone.

17. A medical or dental device for determining a quality of a bone by cutting a thread into the bone by a rotating threaded element having at least one cutting edge, wherein the medical or dental device comprises:
a control unit which comprises
a first electrical contact device for connection to a motor drive,
a second contact device for connection to a display unit, and
a measurement circuit, which is operatively connected to the first electrical contact device and to the second contact device, wherein the measurement circuit is configured:
(i) to determine values of the motor current via the first electrical contact device, the motor current being supplied to the motor drive to rotatably drive the threaded element that can be connected to the motor drive, wherein the motor current values correlate with or are substantially proportional to transmitted torque values of the motor drive, and wherein the motor current values or torque values are a measure of the quality of the bone, and
(ii) to monitor or determine the depth of penetration of the threaded element into the bone,
wherein the control unit is configured to assign to bone quality classes one or more of the determined motor current values, the torque values associated therewith, parameters derived from the motor current values or parameters derived from the torque values and to generate a visual representation of the bone quality classes relative to the depth of penetration.

18. The medical or dental device according to claim 17, wherein the measurement circuit is configured to process angle of rotation values of a rotor of the motor drive in order to monitor or determine the depth of penetration of the threaded element into the bone.

19. The medical or dental device according to claim 17, wherein the measurement circuit is configured to take into account the transmission ratio of a gear unit arranged between the motor drive and the threaded element of the medical or dental device in order to monitor or determine the depth of penetration of the threaded element into the bone.

20. The medical or dental device according to claim 17, wherein the measurement circuit is configured to take into account at least one property of the threaded element in order to monitor and/or determine the depth of penetration of the threaded element into the bone, wherein at least one property of the threaded element comprises at least one of the slope of the at least one cutting edge of the threaded element, the shape of the cutting edge or the outer shape of the cutting element.

21. The medical or dental device according to claim 17, wherein at least one predetermined depth of penetration is stored in the control unit.

22. The medical or dental device according to claim 21, wherein the control unit is configured to compare the monitored or determined depth of penetration of the threaded element with the at least one predetermined depth of penetration and, on reaching or exceeding the at least one predetermined depth of penetration, to stop the motor drive or to change its direction of rotation.

23. The medical or dental device according to claim 17, further comprising a display unit that is communicatively connected to the second contact device and which displays the visual representation of the bone quality classes relative to the depth of penetration.

24. The medical or dental device according to claim 23, wherein the display unit displays the relationship between the depth of penetration and at least one of: the determined motor current values, the torque values which correlate with or are substantially proportional the motor current values, parameters derived from the determined motor current values or parameters derived from the torque values.

25. The medical or dental device according to claim 17, wherein the device additionally comprises a motor drive and a handle element connectable to the threaded element and which is connectable to the motor drive or comprises the motor drive.

26. The medical or dental device according to claim 17, wherein the control unit comprises an evaluation circuit which is configured to compare the motor current values determined by the measurement circuit, the torque values which correlate with or are substantially proportional to the motor current values, parameters derived from the motor current values or parameters derived from the torque values with comparative values for determining the quality of a bone or to assign them into bone quality classes.

\* \* \* \* \*